United States Patent
Esquivel

[11] 3,953,072
[45] Apr. 27, 1976

[54] ORTHOPEDIC CUSHION

[76] Inventor: Salomon Esquivel, 713 Oakwood St., Montebello, Calif. 90640

[22] Filed: Oct. 19, 1973

[21] Appl. No.: 408,171

[52] U.S. Cl. .............................. 297/460; 297/231; 5/345 R
[51] Int. Cl.² .......................................... A47C 3/00
[58] Field of Search ............ 297/231, 232, 454–458, 297/460; 5/345, 355

[56] References Cited
UNITED STATES PATENTS

| | | | |
|---|---|---|---|
| 1,322,292 | 11/1919 | Claus | 297/460 |
| 1,937,920 | 12/1933 | Smith | 297/460 |
| 2,769,485 | 11/1956 | Shapiro | 297/460 |
| 3,205,010 | 9/1965 | Schick | 297/231 |
| 3,222,698 | 12/1965 | Levenson | 5/345 R |
| 3,740,096 | 6/1973 | Bridger | 297/231 |

Primary Examiner—Casmir A. Nunberg
Attorney, Agent, or Firm—J. C. Baisch

[57] ABSTRACT

An orthopedic cushion defined at the front by a wall of fabric material and back and side walls of plastic, said walls defining an enclosure in which is a polyurethane unitary foam filler. The back side of the cushion is substantially flat and planar. The lower part of the cushion is thicker than the upper part and approximately one-third of the way from the bottom, the cushion curves upwardly and rearwardly to a place where it extends upwardly and substantially parallel to the adjacent back wall. The front and back walls above the thickest part of the cushion, are secured together by means of buttons.

2 Claims, 4 Drawing Figures

ORTHOPEDIC CUSHION

BACKGROUND OF THE INVENTION

1. Field of the Invention

The present invention relates to back supporting cushions and relates more particularly to a cushion for helping a lumbar spine distortion and assisting in the healing and correction of muscle tension.

2. Description of the Prior Art

Various cushions have been proposed as a back rest but these generally have not been found to be effective. Further, certain of these prior art devices are complicated in construction.

SUMMARY OF THE INVENTION

An orthopedic cushion defined at the front by a wall of fabric material and back and side walls of plastic, said walls defining an enclosure in which is a polyurethane unitary foam filler. The back side of the cushion is substantially flat and planar. The lower part of the cushion is thicker than the upper part and approximately one-third of the way from the bottom, the cushion curves upwardly and rearwardly to a place where it extends upwardly and substantially parallel to the adjacent back wall. The front and back walls above the thickest part of the cushion, are secured together by means of buttons.

The bottom wall is provided with an opening which extends from side to side of the cushion and this opening is provided with a zipper for gaining access to the interior of the cushion and for closing said opening.

OBJECTS AND ADVANTAGES OF THE INVENTION

It is an object of the present invention to provide an orthopedic cushion for providing proper support for lumbar spine distortion.

It is another object of the invention to provide a cushion of this character that assists in the healing and correction of muscle tension.

Still another object of the invention is to provide a cushion of this character that is simple in construction and effective in use.

The characteristics and advantages of the invention are further sufficiently referred to in connection with the following detailed description of the accompanying drawings, which represent one embodiment. After considering this example, skilled persons will understand that many variations may be made without departing from the principles disclosed and I contemplate the employment of any structures, arrangements or modes of operation that are properly within the scope of the appended claims.

BRIEF DESCRIPTION OF THE DRAWINGS

Referring to the drawings which are for illustrative purposes only.

DESCRIPTION OF THE PREFERRED EMBODIMENTS

Figure 1:
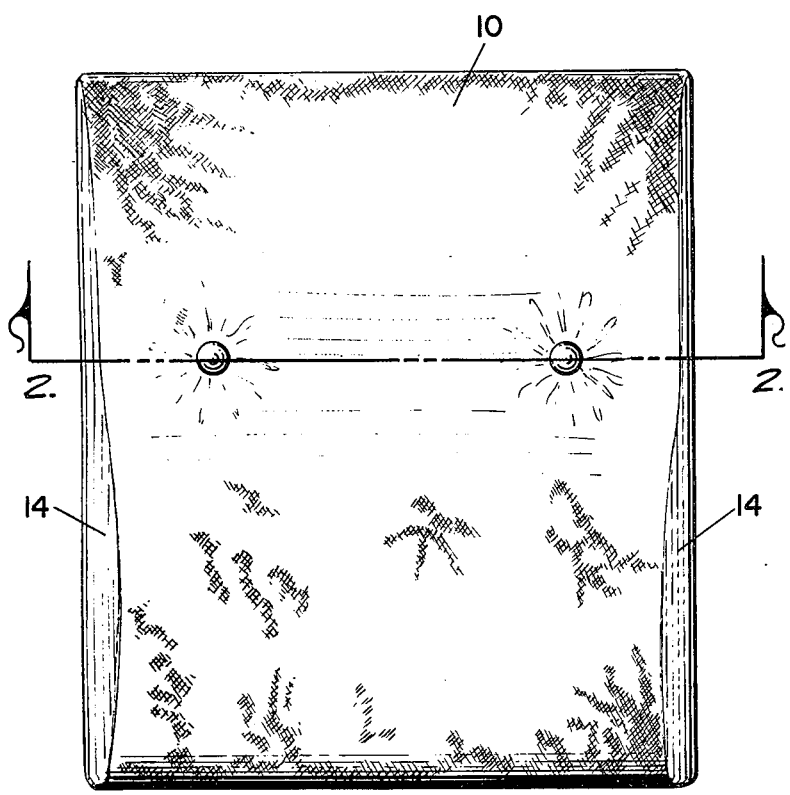
FIG. 1 is a front elevational view of a cushion embodying the present invention.
Figure 2:
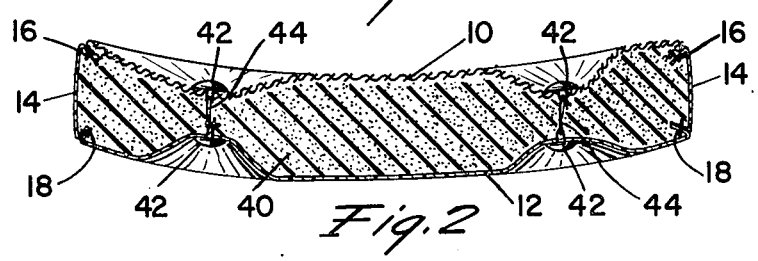
FIG. 2 is a cross-section of the cushion taken on line 2—2 of FIG. 1.
Figure 3:
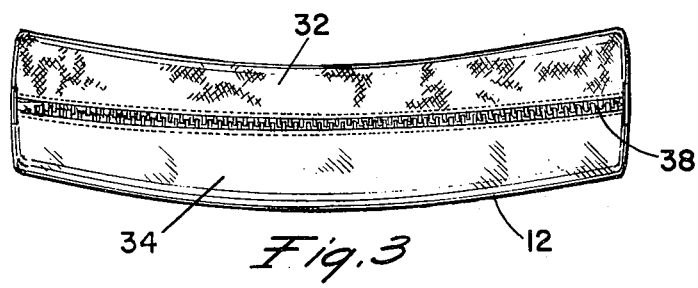
FIG. 3 is a top plane view of the device.
Figure 4:
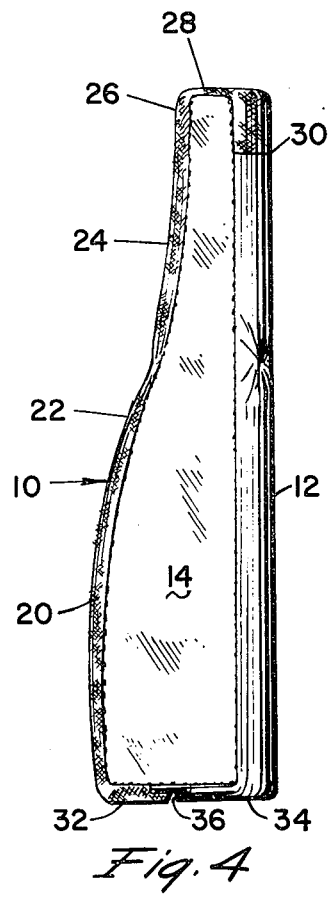
FIG. 4 is a side elevational view thereof.

Referring more particularly to the drawings, there is shown an orthopedic cushion embodying the present invention. The cushion comprises an enclosure having a front wall 10 of a suitable woven fabric or cloth material to permit a breathing passage of air therethrough. There is a back wall 12 of a suitable flexible plastic, there being various well known plastics on the market that are suitable. Side walls 14 are also of flexible plastic and the front and rear edges of said side walls are sewed or otherwise suitably secured to the adjacent edges of the front and back walls as best shown in FIG. 2 at 16 and 18. Side walls 14 have substantially straight back edges while the front edges are wider at the lower part and include a part 20 that is generally parallel to the adjacent part of the rear wall although it does curve slightly forwardly. From this lower part, the front edges of the side walls curve upwardly and toward the rear wall as at 22 and merge into a part 24 that has a slight opposite curvature and terminates in a narrow part or portion 26 at the upper end. The front wall of fabric is turned rearwardly at the upper part of the cushion as at 28 and downwardly a slight distance. The free horizontal edge of the down turned portion of the fabric is sewed as at 30 to the adjacent upper edge of the plastic rear wall 12. The lower edge portion 32 of the front wall is turned rearwardly while a lower edge portion 34 of the back wall is turned forwardly, the transverse edges of said portions 32 and 34 lie adjacent each other to provide an opening 36 for access to the interior of the cushion and a zipper 38 is provided to close this opening. The bottom wall thus formed is substantially flat horizontally to provide a base so that the cushion will be better adapted to stand upright.

Within the cushion, is a body 40 of polyurethane foam having a configuration conforming to the walls of the cushion as above described and the front and rear walls are tied or secured together by buttons 42 interconnected by a cord 44 or the like. This arrangement ensures that the parts of the cushion will be kept in the proper relationship in the assembly. It is to be noted that the cushion is somewhat concavo-convex with the concave side at the front. While the body of resilient foam material 40 is a polyurethane foam, with a ILD (or RMA) No. 33 which is of a medium firm density and is 1.2 lbs. per cubic foot + or minus 0.05, any other suitable material may be used having the foregoing characteristics. This material is sufficiently firm to provide the proper support for the back and yet is resilient or yielding enough to conform to that portion of the back resting against the cushion.

The shape of the front of the cushion is such as to provide help of a lumbar portion of the spine and assist in the healing and correction of muscle tension of this portion of the spine.

The invention and its attendant advantages will be understood from the foregoing description and it will be apparent that various changes may be made in the form, construction and arrangement of the parts without departing from the spirit or scope thereof or sacrificing its material advantages, the arrangement hereinbefore described being merely by way of example and I do not wish to be restricted to the specific form shown or uses mentioned except as defined in the accompanying claims.

I claim:

1. An orthopedic cushion, comprising:
   an enclosure having:
   a front wall of flexible fabric material to permit breathing passage of air therethrough;
   a substantially vertical back wall of flexible plastic material;
   side walls connecting the side edges of the front and back walls, said side walls being relatively wide at the lower portion and tapering inwardly and upwardly and then curving upwardly to a substantially narrower part;
   a top wall closing the upper end of the enclosure;
   a substantially flat bottom wall comprising a rearwardly extending lower portion of the front wall and a forwardly extending lower end portion of the back wall, the free transverse edges of said portions being adjacent each other in defining an elongated opening in said bottom wall, said opening extending transversely of the cushion;
   a unitary body of medium to firm density foam in the enclosure, the vertical section of said material conforming to the shape of the side walls, comprises a bulging part for supporting a portion of the spine for release of muscular tension, said cushion being transversely concavo-convex;
   and means for closing said opening in one of the walls.

2. The invention defined by claim 1, wherein the body of foam material comprises polyurethane foam which is 1.2 lbs. per cubic foot, + or minus 0.05.

* * * * *